United States Patent [19]

Paradissis

[11] Patent Number: 4,764,375

[45] Date of Patent: Aug. 16, 1988

[54] SACHET DRUG DELIVERY SYSTEM

[75] Inventor: George N. Paradissis, St. Louis, Mo.

[73] Assignee: KV Pharmaceutical Company, St. Louis, Mo.

[21] Appl. No.: 775,419

[22] Filed: Sep. 11, 1985

[51] Int. Cl.$^4$ .................. A61K 33/20; A61K 47/00; A61K 9/28

[52] U.S. Cl. .................. 424/153; 424/439; 424/440; 424/498; 514/974; 514/975

[58] Field of Search .................. 424/20, 38, 153, 439, 424/440, 498; 514/974, 975

[56] References Cited

U.S. PATENT DOCUMENTS

| | | | |
|---|---|---|---|
| 2,276,531 | 3/1942 | Wechsler et al. | 514/975 |
| 2,487,336 | 11/1949 | Hinds | 424/498 |
| 2,902,407 | 9/1959 | Gross et al. | 424/498 |
| 3,037,911 | 6/1962 | Stoyle et al. | 424/20 |
| 3,080,292 | 3/1963 | Kolf | 424/20 |
| 3,080,293 | 3/1963 | Kolf | 424/20 |
| 3,138,524 | 6/1964 | Zentner | 514/975 |
| 3,279,994 | 10/1966 | Kolf | 424/20 |
| 3,737,551 | 6/1973 | Karsten et al. | 514/975 |
| 3,780,170 | 12/1973 | Goodhart et al. | 424/498 |
| 4,166,800 | 9/1979 | Fong | 424/497 |
| 4,259,315 | 3/1981 | Lippmann et al. | 424/20 |
| 4,384,975 | 5/1983 | Fong | 424/497 |
| 4,479,911 | 10/1984 | Fong | 424/497 |
| 4,524,060 | 6/1985 | Mughal et al. | 424/20 |
| 4,656,027 | 4/1987 | Sjöovist | 424/495 |

FOREIGN PATENT DOCUMENTS

| | | | |
|---|---|---|---|
| EP179583 | 4/1986 | European Pat. Off. | 514/975 |
| 2549371 | 1/1985 | France | 514/974 |
| 53-148535 | 12/1978 | Japan | 514/975 |

OTHER PUBLICATIONS

The Lancet, Nov. 13, 1982, pp. 1059–1061.
American Druggist, Jan., 1982, p. 44.

Primary Examiner—Ronald W. Griffin
Attorney, Agent, or Firm—Neal Kalishman

[57] ABSTRACT

A drug delivery system in which a taste masked solid is suspended in a liquid carrier. The solid has been rendered hydrophillic and its density approximates that of the carrier liquid.

12 Claims, No Drawings

SACHET DRUG DELIVERY SYSTEM

BACKGROUND OF THE INVENTION

I. Field of the Invention

The invention relates to the delivery of drugs which do not have a palatable taste and where it is undesirable to ingest said drugs in a solid state. Those of ordinary skill in the art would have expertise in taste masking drugs and related products.

II. Description of the Prior Art

Taste masking of drugs through the use of flavors is well known. However, flavoring ingredients are not sufficient to mask certain drugs and vitamins. Therefore, physical means have been developed to encapsulate or place in a chemical barrier these drugs to mask their undesirable taste characteristics.

One such system which has been used for vitamins is disclosed in U.S. Pat. Nos. 3,037,911; 3,080,292; 3,080,293; and 3,279,994. These methods produce products which are in beadlet form. Although these beadlets are effective for taste masking they can cause other difficulties with respect to certain drugs, and types of patients. For instance, patients who have problems taking solid dosage forms cannot utilize drugs produced by this beadlet process.

Also, products, such as, potassium chloride cannot effectively be taken in the beadlet form described by the prior art. Solid forms of potassium chloride are known to lay along the stomach or intestinal lining and ulcerate the stomach or intestinal wall. This ulceration or bleeding of the stomach is a highly undesirable side effect, especially for elderly patients. Thus, the treatment of one affliction causes the occurrence of other serious medical problems.

The present invention is advantageous since it allows the delivery of taste masked particles in a liquid form. It is also advantageous since it is economical and produces a product which has commercially desirable properties. Further it is advantageous since the method of the invention does not effect the active properties of the drug which is being delivered. Other advantages include being able to provide a solid drug form to those who cannot or will not take such drugs especially in large quantities. Finally, it should be noted that the system of the invention meets a long felt need in the art.

SUMMARY OF THE INVENTION

A drug delivery system which taste masks an active agent and prevents gastric ulceration. The system comprises a taste masked solid active agent which has been rendered hydrophillic and whose density approximates that of a carrier liquid in which it is to be suspended.

DESCRIPTION OF THE PREFERRED EMBODIMENTS

The basic particles are produced by the methods disclosed by U.S. Pat. Nos. 3,037,911; 3,080,292; 3,080,293; and 3,279,994. These patents are incorporated by reference herein. The beads produced by these processes are hydrophobic and therefore are unsuitable for use in formulating liquid suspensions.

The beads are formed by pulverizing the active agent. The preferred active agent is potassium chloride which is pulverized to approximately 200 mesh. Waxes or preferably a mixture of mono and diglycerides are melted to a molten state. For glycerides this is approximately 60-80 degrees C. The active agent is added to the melted mixture to form 40-60% of the total.

The waxes and glycerides provide a taste masking coating over the active ingredient. In the present invention the densities of taste masking coating and the active agents are balanced. The total density of the product should equal the density of the liquid into which it is to be suspended. Thus, if the product is to be suspended in water its overall density should approximate 1. Also, ratio of taste masking coating to active agent should be adjusted to reduce the solutility of the drug in the first 60 seconds.

Flavors, modifiers and/or air are added to the mixture. The mixture is placed in a spinner which ejects liquid beads of the mixture which congeals as it cools. The beads are usually 30-100 mesh. They can be compressed into tablet form.

The taste masking coating is hydrophobic and so the beadlets will float on water. In order to render them hydrophillic and improve workability they are blended with surfactants or surface modifiers. A preferred surfactant is sodium lauryl sulfate which forms 0.25 to 2%, preferably 1%, of the beadlet by weight. The surfactant could be added either before or after the spinning of the beads.

Also, additional colors and flavors can be added. Anti-caking agents, such as, silicon dioxide are advantageously added and may comprise 1-3% by weight of the bead. Other materials which do not effect the basic properties of the material may be incorporated into the beadlets. It may be especially desirable to add pH modifiers which reduce dissolution initially but are neutralized by gastric pH. Thereby, allowing rapid dissolution in the stomach.

The beadlets may be packaged in single dose packages. When the patient is required to take a dose, the contents of the package are emptied into a glass of liquid. The beadlets form a suspension and do not dissolve immediately. However, they do dissolve fairly rapidly, 90% within 15 minutes, in order to avoid gastric ulceration. The patient drinks the liquid.

This system has a number of advantages. First, the active ingredient is taste masked as in the solid dosage forms. Second, the liquid can be taken by those who are not capable of taking a solid dosage form. Third, the side effects of the solid dosage form are not encountered. Fourth, gastric ulceration does not occur due to the rapid dissolution of the product. And fifth, a more acceptable consumer delivery system is achieved which encourages patient compliance in taking drugs, especially when large dosages are required.

I claim:

1. A drug delivery system for administering a drug in a liquid form comprising a hydrophillic solid active agent which is taste masked when in a liquid and whose density approximates that of a carrier liquid in which it is suspended.

2. The drug delivery system of claim 1 wherein the ratio of taste mask coating to active agent is such that the solubility in the first 60 seconds of liquid contact is less than that at which the active agent can be tasted.

3. The drug delivery system of claim 1 in which the taste masked active agent dissolves by not less than 90% within 15 minutes following liquid contact.

4. The drug delivery system of claim 1 further comprising flavors.

5. The drug delivery system of claim 1 further comprising surface active agents which promote wetability.

6. The drug delivery system of claim 1 further comprising pH modifiers which reduce dissolution initially but which are neutralized by gastric pH.

7. The drug delivery system of claim 1 wherein said active agent comprises potassium chloride.

8. The drug delivery system of claim 1 wherein said active agent is tastemasked by waxes.

9. The drug delivery system of claim 1 wherein said active agent is tastemasked by a mixture of mono and diglycerides.

10. The drug delivery system of claim 1 further comprising pH modifiers to enhance the physical/chemical stability of the system.

11. The delivery system of claim 1 wherein said solid is approximately 200 mesh.

12. The delivery system of claim 1 wherein said liquid carrier is aqueous.

* * * * *